United States Patent
Pathak et al.

(10) Patent No.: US 6,177,514 B1
(45) Date of Patent: Jan. 23, 2001

(54) BLOCKED FUNCTIONAL REAGANTS FOR CROSS-LINKING BIOLOGICAL TISSUES

(75) Inventors: Chandrashekhar P. Pathak; Mark A. Moore, both of Austin; Richard E. Philips, Jr., San Marcos, all of TX (US)

(73) Assignee: Sulzer Carbomedics Inc., Austin, TX (US)

( * ) Notice: Under 35 U.S.C. 154(b), the term of this patent shall be extended for 0 days.

(21) Appl. No.: 09/289,426

(22) Filed: Apr. 9, 1999

(51) Int. Cl.[7] .................. A61F 2/02; A61F 2/04; A61F 2/06; A61F 2/08; A61F 2/24
(52) U.S. Cl. ............... 525/54.1; 514/12; 600/36; 623/1; 623/2; 623/11; 623/13
(58) Field of Search ................ 525/54.1; 623/1, 623/2, 11, 13; 514/12; 600/36

(56) References Cited

U.S. PATENT DOCUMENTS

| 5,958,669 | * | 9/1999 | Ogle et al. ............ 435/1.1 |
| 6,027,530 | * | 2/2000 | Quintero et al. ........ 623/2 |
| 6,039,760 | * | 3/2000 | Eisenberg ............ 623/15 |

* cited by examiner

*Primary Examiner*—Nathan M. Nutter
(74) *Attorney, Agent, or Firm*—Philip S. Lyeril; Timothy L. Scott

(57) ABSTRACT

A method for cross-linking biological tissue is provided which uses as a cross-linking agent a low molecular weight, substantially monomeric polyfunctional aldehyde formed in situ or just prior to cross-linking. The polyfunctional aldehyde is essentially free of the undesirable heterogeneous polymeric species that result from polyfunctional aldehyde self-reactivity. Also provided is biological tissue that is cross-linked with a substantially monomeric glutaraldehyde.

35 Claims, No Drawings

BLOCKED FUNCTIONAL REAGANTS FOR CROSS-LINKING BIOLOGICAL TISSUES

BACKGROUND OF THE INVENTION

1. Field of the Invention

The present invention relates generally to the field of medical devices for implantation into humans. More particularly, it concerns method for processing biological tissues for use as bioprosthetic devices.

2. Description of the Related Art

Bioprostheses are devices derived from processed biological tissues to be used for implantation into humans. The development of such devices originated as an attempt to circumvent some of the clinical complications associated with the early development of the mechanical heart valve, and has since resulted in a rapid proliferation of bioprosthetic devices for a variety of applications. Examples of some of the bioprostheses currently used or under development include heart valves, vascular grafts, biohybrid vascular grafts, ligament substitutes pericardial patches, etc.

The primary component of the biological tissues used to fabricate bioprostheses is collagen, a generic term for a family of related extracellular proteins. Collagen molecules consists of three chains of poly(amino acids) arranged in a trihelical configuration ending in non-helical carboxyl and amino termini. These collagen molecules assemble to form microfibrils, which in turn assemble into fibrils, resulting in collagen fibers. The amino acids which make up the collagen molecules contain side groups, including amine (NH2), acid (COOH) and hydroxyl (OH) groups, in addition to the amide bonds of the polymer backbone, all of which are sites for potential chemical reaction on these molecules.

Because collagenous tissues degrade very rapidly upon implantation, it is necessary to stabilize the tissue if it is to be used clinically. Chemical stabilization by tissue cross-linking, also referred to as tissue fixation, has been achieved using bi-functional and multi-functional molecules having reactive groups capable of forming irreversible and stable intramolecular and intermolecular chemical bonds with the reactive amino acid side groups present on the collagen molecules.

Glutaraldehyde is the most frequently used agent for cross-linking biological tissues. It is a five carbon aliphatic molecule with an aldehyde at each end of the chain, rendering it bifunctional. These aldehyde groups react under physiological conditions with primary amine groups on collagen molecules resulting in the cross-linking of collagen containing tissues.

Despite its widespread use, there are a number of drawbacks associated with glutaraldehyde cross-linking. For instance, under typical storage conditions, glutaraldehyde is self-reactive and will form a variety of polymeric and other species. As a result, a pure solution of monomeric glutaraldehyde becomes highly heterogeneous over time. The ratio of monomeric to polymeric species, the structure of the glutaraldehyde polymer, its formation kinetics, etc, have been described (for example, see Khor, 1997, and references cited therein).

The presence of polymeric glutaraldehyde species and the general heterogeneity of glutaraldehyde solutions can be problematic in a number of regards. For example, polymeric glutaraldehyde is less tissue permeable than low molecular weight forms. Thus, the use of glutaraldehyde solutions containing highly polymeric species can give rise to tissue that is not uniformly cross-linked, i.e. that contains regions of essentially native tissue within a cross-linked matrix. This non-uniformity can compromise the integrity/durability of the cross-linked tissue for many applications.

Another significant drawback associated with glutaraldehyde cross-linking is the propensity of the treated tissues to undergo calcification. Calcification appears to represent the predominant cause of failure of glutaraldehyde-fixed devices (Golomb et al., 1987; Levy et al., 1986; Thubrikar et al., 1983; Girardot et al., 1995). It is believed that the presence of polymeric forms of glutaraldehyde in the cross-linked tissue may contribute to such calcification, possibly by serving as a physical point of calcification (Thoma et al., 1987). In addition, the non-uniform cross-linking that can result from using heterogeneous glutaraldehyde solutions may also contribute to calcification because exposure of incompletely cross-linked regions following mechanical failure can result in calcification at the rapid rate typical of that for native, non-cross-linked tissue.

Yet another drawback to conventional glutaraldehyde cross-linking is that the polymeric product of glutaraldehyde can depolymize in vivo, causing the release of toxic monomeric glutaraldehyde. This leaching of glutaraldehyde can prevent the cellular growth on the bioprosthesis that is necessary for long term biocompatibility.

Thus, it is a significant disadvantage that polymeric forms of glutaraldehyde are present in the solutions generally used for cross-linking biological tissues. The present invention is directed to overcoming or at least reducing the effects of one or more of the problems set forth above. In particular, a method has been developed in which tissue is fixed with glutaraldehyde, that is in a substantially monomeric form, thereby minimizing the complications associated with the use of heterogeneous glutaraldehyde solutions.

SUMMARY OF THE INVENTION

There is a need within the field of bioprosthetics for simple, cost-effective methods for cross-linking biological tissues which overcome some of the limitations associated with glutaraldehyde cross-linking and which provide bioprosthetic devices with desirable mechanical characteristics and a reduced susceptibility to calcification relative to tissues cross-linked with conventional heterogeneous glutaraldehyde solutions. This invention broadly concerns methods for cross-linking biological tissues, and the cross-linked tissue so produced, by employing a chemical blocking/de-blocking approach to minimize or prevent the presence of undesirable polymeric species of a polyfunctional aldehyde during a cross-linking reaction.

Therefore, according to one aspect of the present invention, the aldehyde groups of a substantially monomeric form of a polyfunctional aldehyde are first chemically blocked so as to provide a non-self-reactive, non-tissue-reactive compound. The blocking groups can be essentially any chemical groups or functionalities that can be reversibly reacted under relatively benign conditions with the aldehyde groups of a polyfunctional aldehyde. Examples of suitable blocking groups include dioxolanes, oximes, imines, oxazolidines, inorganic salts, and the like. The blocked polyfunctional aldehyde is contacted with a biological tissue of interest and removal of the blocking group is effected in situ so as to regenerate a substantially monomeric polyfunctional aldehyde. By incubating the tissue in the presence of the de-blocked polyfunctional aldehyde, cross-linked tissue is thereby provided.

In another aspect of the invention, the de-blocking reaction is not carried out in situ. Rather, a solution is first provided which comprises a substantially monomeric polyfunctional aldehyde, the aldehyde groups of which have been blocked with a blocking group as described above. Removal of the blocking groups regenerates substantially monomeric polyfunctional aldehyde which is thereafter contacted with a biological tissue under conditions effective to result in the desired degree of cross-linking. The tissue is preferably contacted with the solution before a time at which the polyfunctional aldehyde has undergone substantial self-reaction into polymeric species.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Given the self-reactive characteristics of polyfunctional aldehydes, and the undesirability of the presence of polymeric species when using such aldehydes for cross-linking biological tissues, the method according to this invention employs a reversible chemical blocking approach for producing blocked polyfunctional aldehydes that are essentially non-reactive with collagen and non-self-reactive, i.e., non-polymerizable. Upon removal of the blocking groups, polyfunctional aldehyde in a substantially monomeric form is thereby provided. The blocking groups can be removed and the collagen-reactive polyfunctional aldehyde regenerated just prior to performing the cross-linking reaction or, preferably, the polyfunctional aldehyde is regenerated in situ, i.e., within the tissue environment that is to be cross-linked. By ensuring that the aldehyde used in the cross-linking reaction is in a substantially monomeric form, the invention overcomes many of the undesirable features that result from cross-linking tissues with heterogeneous polyfunctional aldehyde solutions.

A polyfunctional aldehyde, as used herein, refers to a molecule that contain two or more aldehyde functionalities. The other constituents present on the molecules are not critical provided they do not adversely effect the ability of the aldehyde groups to be collagen-reactive and thereby capable of producing cross-linked biological tissues. The polyfunctional aldehyde molecule will generally contain an aliphatic component comprising a linear or branched chain having from 2 to about 36 carbon atoms. One illustrative embodiment employs the use of an aldehyde having from 2 to about 10 carbon atoms, such as the linear five-carbon alkyl di-aldehyde, glutaraldehyde. Of course, other like materials having the appropriate aldehyde functionalities may also be used.

The polyfunctional aldehyde is modified such that its aldehyde functional groups are chemically or otherwise blocked with one or more of the disclosed blocking groups in order to minimize or prevent self-reactivity. A blocked aldehyde so produced is a substantially non-reactive (with itself or with tissue), non-polymerizable form of the polyfunctional aldehyde of interest.

Various approaches for reversibly blocking/protecting aldehyde groups from reactivity are known in the art (for example, see Greene and Wuts) and can be used in accordance with this invention. Examples of suitable blocking groups can include, but are not necessarily limited to, inorganic salts such as sodium bisulfite which can form addition products with the polyfunctional aldehydes; dioxolanes such as 1,3-dioxolanes; oximes; oxime derivatives such as O-methyl, O-benzyl, or O-phenylthiomethy; imines; cyclic derivatives such as oxazolidines, etc. The precise make-up of the blocking groups are not critical provided they can be reversibly reacted with the aldehyde groups of the polyfunctional aldehyde and can substantially prevent the polyfunctional aldehyde from self-reacting into polymeric forms during storage.

The blocked aldehydes are converted to a form suitable for cross-linking biological tissues, i.e., to a collagen-reactive form, by effecting removal of their blocking groups. The means by which this "de-blocking" is achieved can vary depending on the nature of the blocking groups used and the chemistry required for their removal. The de-blocking reaction preferably does not result, either directly or indirectly, in an environment that is substantially toxic or denaturing to the tissue, or that otherwise effects in an adverse manner the structure and/or function of the tissue being treated or the cross-linking reaction being performed.

The de-blocking reaction can be performed by essentially any manipulation capable of effecting removal of the blocking groups to regenerate a substantially monomeric polyfunctional aldehyde, or derivatives thereof which possess collagen reactivity. Substantially monomeric means that after the blocking groups have been removed from the blocked aldehyde, there is not a substantial presence of polymeric aldehyde species. By practice of this invention, polymeric species that are present following the de-blocking reaction, i.e. within about 24 hours of the de-blocking reaction, will generally be less than about 20%, more preferably less than about 5%.

pH and/or ionic manipulations may be used in order to effect the de-blocking reaction. This can be accomplished by direct manipulation, such as by modifying the pH of the solution via acid/base additions. For example, when using glutaraldehyde sodium bisulfite salt as the blocked aldehyde, de-blocking may be achieved by either an increase or a decrease in the pH. The extent to which the pH will need to be adjusted to effect de-blocking will, of course, vary depending on the specifics of the application, such as the tissue being treated and the aldehyde and blocking agents employed. However, the preferred pH conditions for de-blocking can be readily determined by the skilled individual in the art.

Alternatively, the de-blocking reaction can be effected by other suitable physical or chemical stimuli that may be effective for the particular blocking/de-blocking chemistries being employed. For example, these could include light induced manipulations of pH, e.g., strong acids can be generated by photochemical reaction of iodinium salts.

Although optimal conditions for a tissue cross-linking reaction may vary, the reaction is generally tolerant of a reasonably wide range of pH and other solution characteristics. In many instances, the reaction will proceed in the same environment that is used for the de-blocking reaction. In other situations, however, routine experimental optimization may be necessary and/or preferred in order to modify the solution after de-blocking so as to achieve reaction conditions that are most conducive with optimal cross-linking kinetics.

The de-blocking reaction is preferably carried out in situ, i.e., in the presence of the tissue that is to be cross-linked.

This can be accomplished by first contacting a biological tissue with a blocked aldehyde solution, preferably by immersion of the tissue in the solution. The blocked aldehyde should be essentially non-reactive with the tissue. As a result, the tissue can be left in the solution for extended periods if necessary or desired. In order to initiate the cross-linking reaction, the blocked aldehyde is de-blocked and the polyftnctional aldehyde is thereby regenerated in the presence of the tissue. This results in the in situ production of substantially monomeric collagen-reactive polyfunctional aldehyde for participation in tissue cross-linking.

The non-reactivity of a blocked aldehyde is advantageous in the event that the de-blocking reaction is incomplete, since residual blocked aldehyde is tolerated by the biological tissue. Alternatively, any unreacted aldehydes present within the cross-linked tissue may be converted back to the blocked form if desired. For instance, if the cross-linked tissue is treated with sodium bisulfite, it could react with any unreacted aldehyde groups within the tissue. The negative charge of the resulting aldehyde bisulfite groups may improve the biocompatibility of the cross-linked tissue.

As an alternative to an in situ de-blocking reaction, a blocked aldehyde can be first de-blocked and this de-blocked solution can thereafter be contacted with the biological tissue to be cross-linked. The de-blocked solution is used prior to a time at which substantial polymerization of the aldehyde has occurred. Preferably, the tissue is contacted with the solution within about one week of de-blocking, more preferably, within about one day of de-blocking, most preferably within about six hours of de-blocking, in order to minimize the undesirable formation of polymeric species of the aldehyde.

Inorganic salt forms of glutaraldehyde, such as glutaraldehyde sodium bisulfite, are well suited for use as blocked aldehydes. The de-blocking reaction of many such compounds can be carried out under relatively mild reaction conditions which are easily tolerated by the tissue. The de-blocking groups are water soluble and inorganic in nature and thus can be readily removed after the reaction. In addition, the blocked reagant is non-tissue reactive and water soluble and can readily penetrate the tissue of interest.

One illustrative blocked polyftnctional aldehyde for use in the invention is formed as a result of reaction of a polyfunctional aldehyde with sodium bisulfite or another suitable inorganic salt. The aldehyde groups of a polyfunctional aldehyde react with sodium bisulfite as illustrated below

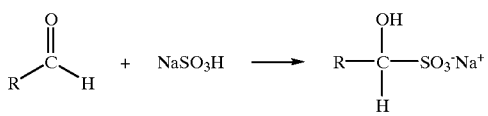

The aldehyde bisulfite addition compounds that result from such a reaction are useful as blocked polyfunctional aldehydes according to this invention. These compounds are not substantially tissue-reactive or self-reactive, can be purchased in commercially available forms, and can be easily de-blocked in situ by a relatively benign and straightforward manipulation of solution pH.

Another illustative blocked polyfunctional aldehyde for use in this invention may be formed by reaction of the aldehyde groups of a polyfunctional aldehyde to form dioxolane or dioxolane derivatives. For example, 2,2'-trimethylenebis-1,3-dioxolane may be used as a blocked polyfunctional aldehyde, as illustrated below.

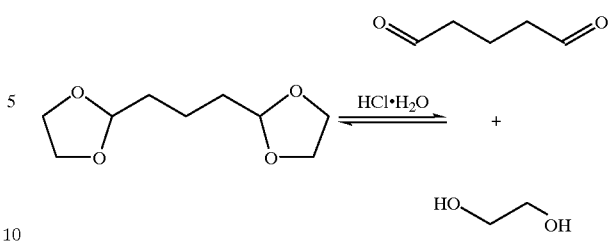

This dioxolane, and related compounds, can be easily de-blocked to form monomeric glutaraldehyde by lowering the pH of the solution. A tissue sample can then be cross-linked by contacting the tissue with the monomeric glutaraldehyde so produced. Generally, as with most de-blocking reactions which result in the monomeric polyfunctional aldehyde being present under acidic pH conditions, it may be desired to re-adjust the pH of the solution after the de-blocking reaction so as to provide a pH sufficiently high (e.g., a physiological or slightly basic pH) to provide the tissue cross-linking desired for a given application.

The skilled individual in this art will recognize that the length of the cross-linking reaction according to this invention is not critical so long as the tissue and the cross-linking agent remain in contact for a time sufficient to allow the desired degree of cross-linking to occur. Time of treatment may vary depending on the type of tissue being treated and/or the particular polyfunctional aldehyde and de-blocking reaction used. Typically, the length of the reaction will be from about one minute to several days. However, the time of treatment should not be so long as to adversely effect the cross-linked tissue. Thus, cross-linking times greater than about one or two days are generally avoided. Preferably, the tissue is treated for a period from about one minute to about twelve hours, more preferably for about one hour to six hours. The degree of cross-linking can to some extent be varied by the length of time the reaction is allowed to proceed.

Suitable reaction temperatures and/or pressures include those that are effective for allowing the desired cross-linking reaction to occur while not adversely compromising the progression of the cross-linking reaction or the integrity of the tissue being treated. Identification of optimal temperature and pressure conditions for a particular agent and/or application can be readily determined by the skilled individual in this art. Generally, the cross-linking reaction can be carried out at an ambient temperature or at any other convenient temperature provided it does not substantially exceed the tissue denaturation temperature of about 62 deg.C. Thus, suitable reaction temperatures for use in this invention may range from about 0 deg.C. to about 60 deg.C., preferably from about 20 deg.C to about 50 deg.C. Although the pressure for a typical reaction generally ranges from about 2 to about 6 mm Hg, suitable pressures may be as high as 100 mm Hg or more, if desired.

After the cross-linking reaction has proceeded for a time and under conditions effective for providing the desired degree of cross-linking, the tissue is generally washed several times prior to implantation. This can be carried out with water, alcohol, or other suitable washing solutions known in the art.

Various types of implantable biological tissues derived from numerous animal sources and parts of the anatomy can be treated in accordance with this invention. Thus, the tissue can be derived from sources such as human, bovine, porcine, equine, sheep, kangaroo, rabbit etc., and can include such things as tendons, ligaments, heart valves, tissues to construct heart valves such as dura matter and pericardium, vascular grafts, biohybrid vascular grafts, patches, etc. For some applications, it may be desired to manipulate the tissue in some manner so as to provide it in a particular form/shape, for example using metallic stents, prior to the cross-linking reaction. In this way, the tissue may be cross-linked in the particular three-dimensional geometric configuration of the bioprosthesis to be implanted.

The following examples are provided to demonstrate certain illustrative embodiments of this invention. It should be appreciated by those skilled in the art that the techniques disclosed in the examples which follow represent those found by the inventors to function in the practice of the invention and thus can be considered to constitute examples of particular modes for its practice. However, those skilled in the art should, in light of the present disclosure, appreciate that many changes can be made in the specific embodiments which are disclosed and still obtain a like or similar result without departing from the spirit and scope of the invention.

EXAMPLE 1

Bovine pericardium samples (having diameter of approximately 1 cm) were treated with either water, commercially available glutaraldehyde, glutaraldehyde sodium bisulfite (Aldrich; Milwaukee, Wis.), or glutaraldehyde sodium bisulfite into which an equivalent quantity of sodium hydroxide solution was added after the tissue had already been immersed. Pericardium tissue was first suspended in 10 ml distilled water in a 20 ml glass vial followed by the addition of the desired cross-linking agent, as indicated in Table 1. The vials were vortexed and the reactions were run for about 6 hours at ambient temperature. They were subsequently washed with water, then with 50% ethanol several times, and stored under refrigeration prior to analysis.

A protein extraction assay was performed in order to evaluate the progress of the cross-linking reactions under these conditions. Cross-linking of the tissue results in less extractable protein from the biomaterial. These assays were performed by extracting 10–20 mg of tissue with 10–20 ul of an extraction solution containing 50 mM Tris-HCl, 10% glycerol, 4% mercaptoethanol, 1% sodium dodecyl sulfate, 0.5M NaCl and 0.01% bromophenol blue. The extracted solution was then analyzed on a 4–20% acrylamide:bisacrylamide (37.5:1) Mini-PROTEAN II ready Gel (Biorad; Richmond, Calif.).

The shrinkage temperatures of the treated tissues were also determined using standard differential scanning calorimetric analysis. Typically, 2–10 mg of tissue was heated at the rate of 10 deg.C. per minute under nitrogen atmosphere. The onset of the endotherm observed at about 60–80 deg.C. was used as the shrinkage temperature. An increase in the shrinkage temperature is an indication that cross-linking has occurred.

The results of these experiments are presented in Table 1 below:

TABLE 1

| SAMPLE | TREATMENT | EXTRACTABLE PROTEIN | SHRINK TEMPERATURE |
| --- | --- | --- | --- |
| Untreated | 10 ml H2O | Present | 64.5 ± 0.0 |
| Glutaraldehyde (GA) | 10 ml 0.25% GA solution. | Absent | 82.3 ± 0.4 |
| Glutaraldehyde Sodium Bisulfite (BS) | 10 ml H2O 0.062 g BS | Present | 64.2 ± 0.2 |
| Glutaraldehyde Sodium Bisulfite (BS) + NaOH | 10 ml H2O 0.062 g BS 0.066 ml 3N NaOH | Absent | 76.0 ± 0.4 |

Thus, samples treated with glutaraldehyde sodium bisulfite into which NaOH was added effectively regenerated glutaraldehyde in situ. The regenerated aldehyde so produced was available for participation in the cross-linking of the pericardial tissue, as evidenced by the absence of extractable protein and by the increase in shrink temperature.

EXAMPLE 2

A solution of 2,2'-trimethylenebis-1,3-dioxolane (Aldrich Chemical; #27,201-9) was prepared to a concentration of 0.05M by adding 85 $\mu$l of 2,2'-trimethylenebis-1,3-dioxolane in 5 ml of PBS to 5 ml of ethanol. The solution was analyzed spectrophotometrically between 200 nm and 350 nm (Shimadzu UV160 Spectrophotometer). The solution showed only a very small peak at 280 nm, indicating the substantial absence of free (i.e., de-blocked) monomeric glutaraldehyde.

In order to de-block the 2,2'-trimethylenebis-1,3-dioxolane, 10 ul of 12N hydrochloric acid was added to 1 ml of the 2,2'-trimethylenebis-1,3-dioxolane. The reaction was allowed to proceed at room temperature for about 1 hour. The sample was then analyzed spectrophotometrically. A monomeric glutaraldehyde peak at 280 nm was observed that was comparable to a monomeric glutaraldehyde peak observed for a 0.25% glutaraldehyde solution (not shown). These results demonstrate that a polyfunctional aldehyde blocked with a dioxolane can be effectively de-blocked by lowering the pH of the solutions so as to generate monomeric glutaraldehyde.

EXAMPLE 3

Bovine pericardium tissue samples were cut into circular samples (diameter ~1 cm) and contacted with 5 ml of one of the following:

(1) phosphate buffered saline, pH 7.3 (PBS);

(2) 50% ethanol in PBS;

(3) 0.05 M 2,2'-trimethylenebis-1,3-dioxolane in 50% ethanol/PBS;

(4) 0.05M 2,2'-trimethylenebis-1,3-dioxolane in 50% ethanol/PBS, reacted with HCl for 1 hour; or (5) 0.05M 2,2'-trimethylenebis-1,3-dioxolane in 50% ethanol/PBS, reacted with HCl for 1 hour and then pH adjusted to 7.3.

The tissue samples were incubated in the above solutions at room temperature for about six hours, washed three times with PBS, and stored in 50% ethanol/PBS. To evaluate whether crosslinking had occurred in the tissue samples, protein extraction and differential scanning calorimetry analyses were performed, as described in Example 1. The results of these experiments are summarized below in Table 2.

TABLE 2

| TREATMENT | EXTRACTABLE PROTEIN | SHRINK TEMPERATURE |
|---|---|---|
| (1) PBS, pH 7.3 | Present | 66.3 |
| (2) 50% ethanol/PBS | Present | 68.3 |
| (3) 2,2'-trimethylenebis-1,3-dioxolane | Present | 66.0 |
| (4) 2,2'-trimethylenebis-1,3-dioxylane + HCl | Present | 63.0 |
| (5) 2,2'-trimethylenebis-1,3-dioxylane + HCl, pH adjusted to 7.3 | Absent | 71.5 |

These results demonstrate that after de-blocking a dioxolane-blocked polyfunctional aldehyde, the de-blocked aldehyde is effective for cross-linking biological tissue provided that the pH of the reaction solution is one that is conducive with the cross-linking reaction, e.g., a neutral or slightly basic pH.

The particular embodiments disclosed above are illustrative only, as the invention may be modified and practiced in different but equivalent manners apparent to those skilled in the art having the benefit of the teachings herein. More specifically, it will be apparent that certain agents which are chemically and/or physiologically related may be substituted for the agents described herein while the same or similar results would be achieved. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

REFERENCES

The following references, to the extent that they provide exemplary procedural or other details supplementary to those set forth herein, are specifically incorporated herein by reference.

Girardot et al., J Biomed Mater Res (1995) 29: 793–801
Golomb et al., Am J Pathol (1987) 127: 122–130
Greene and Wuts, In: Protective Groups in Organic Synthesis; John-Wiley and Sons, 175–217
Khor, Biomaterials (1997) 18:95–105
Levy et al., In: CRC Critical Rev. in Biocompatibility, Williams D F, ed., Vol. 2 (1986): 147–187
Thoma et al., J Biomat. App. (1987) 1: 449
Thubrikar et al., J Thorac Cardiovasc Surg (1983) 86: 115–125

What is claimed:

1. A method for cross-linking biological tissue comprising:
  (a) contacting a biological tissue with a solution comprising a polyfunctional aldehyde, wherein the aldehyde groups of said polyfunctional aldehyde have been blocked with a blocking group selected from the group consisting of dioxolanes, oximes, imines, oxazolidines, and inorganic salts;
  (b) removing the blocking groups from said polyfunctional aldehyde to regenerate substantially monomeric polyfunctional aldehyde; and
  (c) incubating the biological tissue for between 1 min and 2 days.

2. The method of claim 1, wherein the polyfunctional aldehyde contains a linear or branched aliphatic component having 2–36 carbon atoms.

3. The method of claim 1, wherein the polyfunctional aldehyde contains a linear or branched aliphatic chain having 2–10 carbon atoms.

4. The method of claim 1, wherein the aldehyde groups of said polyfunctional aldehyde are blocked with a blocking group comprising sodium bisulfite.

5. The method of claim 1, wherein the aldehyde groups of said polyfunctional aldehyde are blocked with a blocking group comprising a 1,3-dioxolane.

6. The method of claim 1, wherein the polyfunctional aldehyde is glutaraldehyde.

7. The method of claim 1, wherein removing the blocking group is achieved by effecting a change in the pH of the solution.

8. The method of claim 1, wherein biological tissue is a prosthetic heart valve, vascular graft, tendon, ligament, or patch.

9. Cross-linked biological tissue produced according to the method of claim 1.

10. A method for cross-linking biological tissue comprising:
  (a) providing a solution comprising a polyfunctional aldehyde, wherein the aldehyde groups of said polyfunctional aldehyde have been blocked with a blocking group selected from the group consisting of dioxolanes, oximes, imines, oxazolidines, and inorganic salts;
  (b) removing the blocking groups so as to regenerate substantially monomeric polyfunctional aldehyde;
  (c) contacting the solution with a biological tissue for between 1 min and 2 days.

11. The method of claim 10, wherein the polyfunctional aldehyde contains a linear or branched aliphatic component having 2–36 carbon atoms.

12. The method of claim 10, wherein the polyfinctional aldehyde contains a linear or branched aliphatic component having 2–10 carbon atoms.

13. The method of claim 10, wherein the aldehyde groups of said polyfunctional aldehyde are blocked with a blocking group comprising sodium bisulfite.

14. The method of claim 10, wherein the aldehyde groups of said polyfunctional aldehyde are blocked with a blocking group comprising a 1,3-dioxolane.

15. The method of claim 10, wherein the polyfunctional aldehyde is glutaraldehyde.

16. The method of claim 10, wherein removing the blocking group is achieved by effecting a change in the pH of the solution.

17. The method of claim 10, wherein biological tissue is a prosthetic heart valve, vascular graft, tendon, ligament, or patch.

18. The method of claim 10, wherein step (c) is performed within 24 hours of step (b).

19. The method of claim 10, wherein step (c) is performed within 6 hours of step (b).

20. The method of claim 10, wherein step (c) is performed within 1 hours of step (b).

21. Cross-linked biological tissue produced according to claim 10.

22. A biological tissue comprising collagen that is cross-linked with a substantially monomeric polyfunctional aldehyde.

23. The biological tissue of claim 22, wherein less than 10% of the polyfunctional aldehyde present in the tissue is in a polymeric form.

24. The biological tissue of claim 22, wherein less than 5% of the polyfunctional aldehyde present in the tissue is in a polymeric form.

25. A method for cross-linking biological tissue comprising:
   (a) providing a solution comprising a polyfunctional aldehyde, wherein the aldehyde groups of said polyfunctional aldehyde have been blocked with a blocking group selected from the group consisting of dioxolane and sodium bisulfite;
   (b) removing the blocking groups so as to regenerate substantially monomeric polyfunctional aldehyde;
   (c) contacting the solution with a biological tissue for between 1 min and 2 days.

26. The method of claim 25, wherein the polyfunctional aldehyde contains a linear or branched aliphatic component having 2–36 carbon atoms.

27. The method of claim 25, wherein the polyfunctional aldehyde contains a linear or branched aliphatic chain having 2–10 carbon atoms.

28. The method of claim 25, wherein the aldehyde groups of said polyfunctional aldehyde are blocked with a blocking group comprising a 1,3-dioxolane.

29. The method of claim 25, wherein the polyfunctional aldehyde is glutaraldehyde.

30. The method of claim 25, wherein removing the blocking group is achieved by effecting a change in the pH of the solution.

31. The method of claim 25, wherein biological tissue is a prosthetic heart valve, vascular graft, tendon, ligament, or patch.

32. Cross-linked biological tissue produced according to the method of claim 25.

33. The method of claim 1, wherein said incubating step occurs for between 1 hr and 6 hr.

34. The method of claim 10, wherein said contacting step occurs for between 1 hr and 6 hr.

35. The method of claim 25, wherein said contacting step occurs for between 1 hr and 6 hr.

* * * * *